United States Patent
Robinson

(10) Patent No.: US 6,333,056 B1
(45) Date of Patent: Dec. 25, 2001

(54) HERBAL-BASED PHARMACEUTICAL FORMULATIONS

(76) Inventor: Ralph Stanley Robinson, 61 Lewis Rd., Guelph Ontario (CA), N1H 1E9

( * ) Notice: Subject to any disclaimer, the term of this patent is extended or adjusted under 35 U.S.C. 154(b) by 0 days.

(21) Appl. No.: 09/781,547

(22) Filed: Feb. 13, 2001

Related U.S. Application Data

(63) Continuation of application No. 09/636,824, filed on Aug. 14, 2000, now abandoned.

(51) Int. Cl.⁷ .................................................... A61K 35/78
(52) U.S. Cl. ................................................... 424/725
(58) Field of Search ............................... 424/725

(56) References Cited

U.S. PATENT DOCUMENTS

| | | | | |
|---|---|---|---|---|
| 4,440,760 | * | 4/1984 | Newnham | 424/184 |
| 4,670,263 | * | 6/1987 | Noorlander | 424/195.1 |
| 5,707,631 | * | 1/1998 | Lieberman et al. | 424/195.1 |

\* cited by examiner

*Primary Examiner*—Raymond Henley, III
(74) *Attorney, Agent, or Firm*—Robert G. Hirons

(57) ABSTRACT

A herbal based formulation for treatment of horses and dogs to alleviate the symptoms of osteoarthritis comprises a mixture of devils claw and comfrey, preferably also including dandelion, burdock and nettles, as an intimate admixture, added to the animal's feed.

19 Claims, 2 Drawing Sheets

HERBAL-BASED PHARMACEUTICAL FORMULATIONS

CROSS-REFERENCE TO RELATED APPLICATION

Figure 1:
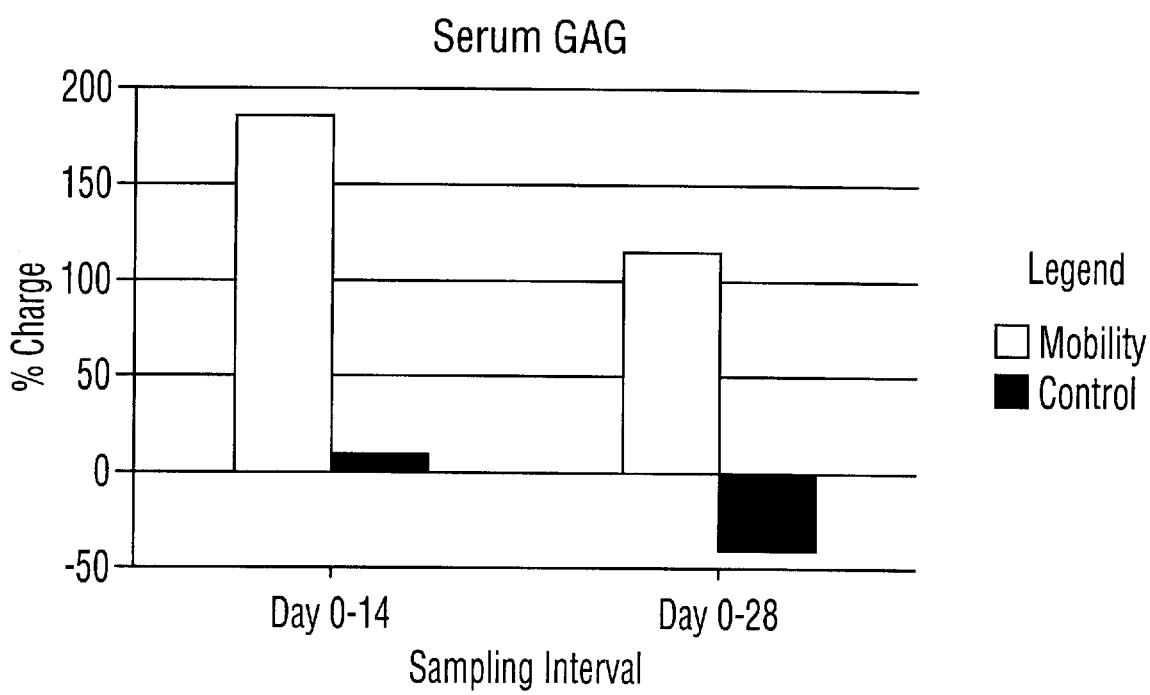

This is a continuation of U.S. patent application Ser. No. 09/636,824 filed Aug. 14, 2000, now abandoned, the entire disclosure of which is incorporated herein by reference.

FIELD OF THE INVENTION

This invention relates to pharmaceutical formulations and methods for their preparation and use. More specifically, it relates to herbal-based preparations useful for administration to animals, especially horses and dogs, for alleviation of the symptoms of arthritis.

BACKGROUND OF THE INVENTION AND PRIOR ART

Osteoarthritis is a degenerative disease of the joints which affects a large number of horses, and accounts for a considerable economic burden on the equine industry. A wide variety of pathological episodes in the equine joint, such as lameness, can culminate in the common end stage of osteoarthritis. The condition is typified by progressive deterioration of the articular cartilage, accompanied by changes in the bone and soft tissue of the joint, and eventual loss of joint function.

Osteoarthritis in equine and canine patients is commonly treated with non-steroidal anti-inflammatory drugs (NSAIDs), and steroids. This method of treatment elicits large scale, clinical improvement in equine and canine patients, but there is concern over potential side effects to chronic use. For example, NSAIDs used over the long term have been implicated in gastric ulceration, and inhibition of chondrocyte metabolism. Corticosteroids have been reported to reduce hyaluronic acid synthesis and chondrocyte metabolism, and other suspected side effects.

Accordingly, herbal remedies for mitigation of various inflammatory conditions are increasingly being sought. Reports for the most part are anecdotal, although there are a number of scientific documentations for herbs' actions in vitro and in some laboratory animals. A recent survey of more than 1000 trainers, owners, breeders and veterinarians in the Ontario horse industry highlighted their calls for more research into natural therapeutics. A lack of information on alternative therapies was second only to respiratory disease as the number one horse-health issue facing the industry.

It is an object of the present invention to provide a novel formulation, based on natural products, useful for treatment of arthritis in horses and/or in dogs.

SUMMARY OF THE INVENTION

According to one aspect of the present invention, there is provided a herbal based formulation for administration to mammals to alleviate symptoms of arthritis, and comprising an intimate admixture of at least two different plant ingredients, said plant ingredients being an effective amount of a plant material providing a rich source of harpagosides, and an effective amount of a plant material providing a rich source of allantoin.

Another aspect of the present invention is a process of alleviating symptoms of osteoarthritis in equine and canine patients, which comprises administering to the patient an effective amount of the herbal formulation defined above.

BRIEF REFERENCE TO THE DRAWINGS

Figure 2:
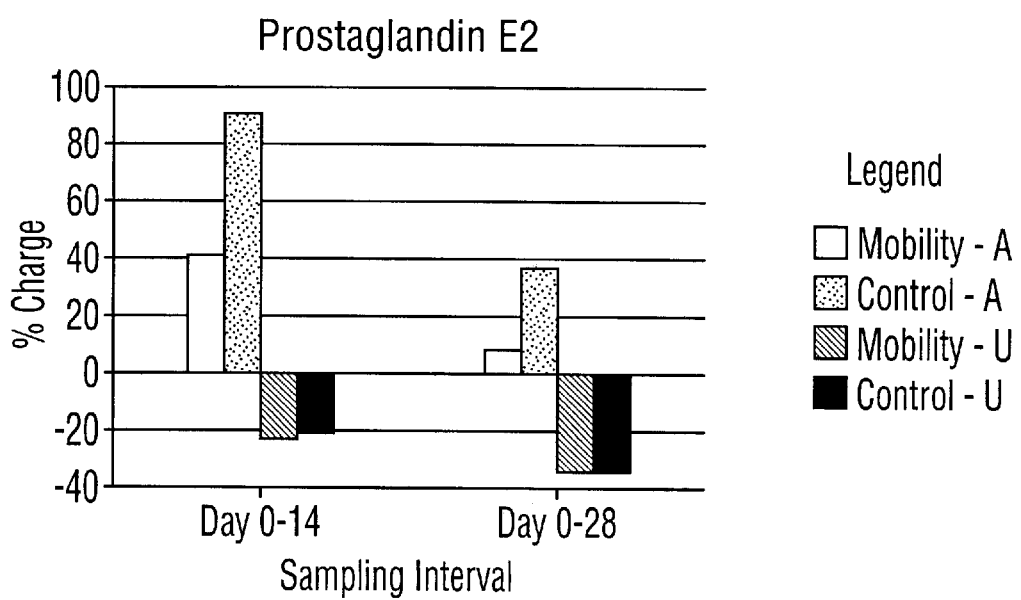
Figure 3:
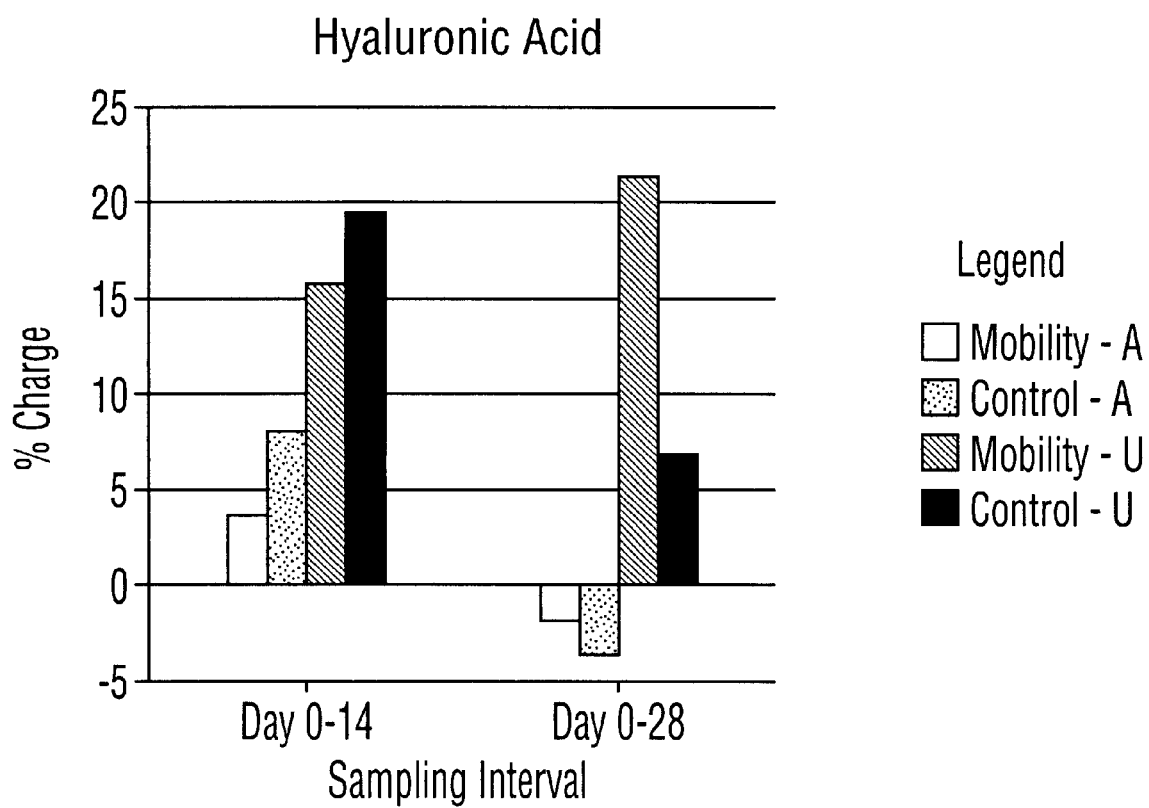

FIG. 1 of the accompanying drawings in a graphical presentation of the experimental results obtained according to Example 2 below, namely a plot of serum glycosaminoglycans in blood of horses fed a composition according to the invention, against time of sampling;

FIG. 2 thereof is a graphical presentation of further experimental results from Example 2 below, namely a plot of prostaglandin $E_2$ levels in synovial fluid of horses fed a composition according to the invention, against time of sampling; and FIG. 3 thereof is a graphical presentation of further results of Example 2, namely a plot of hyaluronic acid content of synovial fluid of horses fed a composition according to the invention, against time of sampling.

DESCRIPTION OF THE PREFERRED EMBODIMENTS

A preferred example of a plant material providing a rich source of harpagosides is *harpagophytum* (devils claw). A preferred example of a plant material providing a rich source of allantoin is *Symphytum officinalis* (comfrey). Suitable relative proportions of these two ingredients are, by weight, from about 10–30 parts of devil's claw and from about 10–30 parts by weight of comfrey.

A preferred formulation according to the invention includes, in addition to the above ingredients, from about 5 to 10 parts by weight of a plant material providing a rich source of steroidal saponins, for example *schidegara* (yucca); and from about 5 to 20 parts by weight of a plant material from the plant Boswellia.

The plant material used in the formulations of the present invention may be the leaves, the roots, the seeds, the tubers, the pods or the stalks of the plant in question, or, indeed the whole plant, depending upon where in the respective plant the active ingredient is found in high concentration. In the case of devils claw, it is preferred to use the tuber. With comfrey, yucca and boswellia, the leaves, after suitable drying, are preferably used.

Another preferred formulation according to the present invention herbal based formulation for administration to animals to alleviate symptoms of arthritis, and containing at least five different plant ingredients, said plant ingredients being:

from about 10 to 30 parts by weight of a plant material providing a rich source of harpagosides, for example *harpagophytum* (devils claw);

from about 10 to 30 parts by weight of a plant material providing a rich source of allantoin, for example *Symphytum officinalis* (comfrey);

from about 10 to 30 parts by weight of a plant material providing a rich source of taraxacin and sterols, for example *Taraxacum officinalis* (dandelion);

from about 10 to 30 parts by weight of a plant material providing a rich source of glycosides, for example *Arcticum lappe* (burdock);

and from about 10–30 parts by weight of a plant material providing a rich source of histamines, for example *Urtica dioica* (nettles).

An especially preferred formulation according to the present invention may include all of the above recited ingredients, in the specified relative proportions.

The most useful parts of the dandelion for the formulations of the invention are the roots and leaves. For burdock, it is preferred to use roots. With nettle, the whole plant is suitably used.

The formulations are simply and conveniently prepared by a dry mixing procedure. The selected parts of the plants are chopped to small size and dried in warm air, to a moisture content of less than about 5%. Then the formulations are prepared by dry mixing of appropriate weighed quantities of the dried, finely divided materials, until a substantially homogeneous mixture is obtained.

Administration of the formulations to the animals is preferably as a dry feed supplement, a measured quantity of the formulation being added to the animals' morning and/or evening grain ration. Flavor enhancers may be added, to encourage the animals' ingestion of the formulation. Suitable approximate quantities of formulation are from about 4–12 ounces of formulation, dry weight, daily, per 1000 pounds body weight of the animal. Positive results in the alleviation of pain and inflammation due to osteoarthritis are generally observed after about 7 days of such administration of formulation.

The formulations of the present invention provide a rich source of various phytochemicals for the animal patient. It is believed that the combined action of these phytochemicals, much of the combined action being synergistic in nature, is responsible for the anti-arthritic effects obtained from the formulations. These phytochemicals are, broadly, glycosides, flavonoids, allantoin, mucilage and sesquiterpenes. A plant material noted herein as providing "a rich source" of a specific phytochemical should be understood to mean a content of that phytochemical in the specific plant material such as leaves, roots, tubers, etc. of at least 0.05% and preferably at least 0.1% dry weight of the phytochemical, in physiologically active form, based on the dry weight of the plant material in which it is found. Other plant ingredients beside the phytochemicals may also play a beneficial role, as is believed to occur with administration of various other types of herbal medicines.

The mechanism of action of the formulations of the present invention appears to be through the regulation of the generation of the highly effective inflammatory agent prostaglandin $E_2$, $PGE_2$. This molecule is an oxidation product of arachidonic acid—a reaction which is catalyzed by the enzyme cyclooxygenase. $PGE_2$ is a potent vasodilator, and hyperalgesic. The vasodilator action occurs through the synergism between $PGE_2$ and other mediators including bradykinin and histamine, and the result is an increase in vascular permeability and erythema. This causes the characteristic hypersensitivity to pain observed in inflammatory conditions. In addition, there is important synergism between $PEG_2$ and the cytokine IL-1. This cytokine is present in articular joints, and its production is controlled by mRNA. However, during osteoarthritis, the level of IL-1 in articular cartilage is elevated and it promotes breakdown of the proteoglycans that make up the cartilage matrix. It is often accompanied by an increase in $PGE_2$, and together they work to exacerbate the degenerative process by stimulating the release of metalloproteinases—enzymes which catalyze articular cartilage catabolism.

The formulations of the present invention reduce the production of $PGE_2$, and consequently appear to inhibit the hypersensitivity to pain, and to suppress the ongoing degradation of articular cartilage. Thus, while present indications are that the success of the formulations of the present invention are associated with inhibition in the production of $PGE_2$, the present invention is not to be interpreted as limited to any specific theory or mode of action.

The invention is further described, for illustrative purposes, with reference to the following specific examples.

EXAMPLE 1

The formulation used in the examples (clinical trials) had the composition given in Table 1.

TABLE 1

| Composition | | | |
|---|---|---|---|
| Plant | Scientific Name | Parts Used | Quantity (parts by wt) |
| Dandelion | Taraxacum officinalis | roots, leaves | 20 |
| Devil's Claw | Harpagophytum procumbens | tuber | 20 |
| Comfrey | Symphytum officinalis | leaves | 20 |
| Burdock | Arctium lappa | leaves, seeds, pods, roots | 20 |
| Stinging Nettle | Urtica dioica | whole plant | 20 |

To prepare the formulation, the harvested plant parts were dried in an air-flow oven at 80° C. until constant weight was achieved and the moisture content thereof was less than 5% by weight. Then the plant parts were chopped to small size, and intimately mixed together in a dry blender, in the proportions set out above, to achieve a dry, uniform, homogeneous, free-flowing solid mixture.

EXAMPLE 2

The formulation prepared in Example 1 was fed to 6 horses (4 thoroughbred, 2 standard bred) suffering from clinical lameness together with at least one other indicator of osteoarthritis (i.e. history of chronic lameness, positive flexion and/or positive radiographs. Horses and selection criteria are listed in Table 2, along with results of the tests described below.

Horses were stabled and fed a sweet feed and free-choice of hay ration, which met the horses' nutritional requirements. Horses were given a minimum two week acclimatization period at the stables. The horses were randomly assigned to two groups I and II, of equal numbers. In phase A of the trial, the horses of Group I were fed a normal morning and evening grain ration but additionally containing ½ cup of the herbal mixture from Example 1. During phase A, the horses of Group II were given normal grain rations morning and evenings supplemented with ½ cup of alfalfa (placebo). At the end of phase A, which lasted 28 days, horses were given a 21 day "washing out" period, during which no supplement was fed. The horses were then crossed over, and the regime was repeated (Phase B) with the Group II horses receiving the herbal mixture and the Group I horses receiving placebo, in the same amounts and frequencies. for 28 days. In this way, each horse acted as its own control. The researchers were blinded to the herbal mixture and the placebo.

Horses were turned out daily, and stabled at night. Observation of lameness and flexion of the deficient joint were made and recorded at the start and at the end of the courses of treatment.

TABLE 2

Selection Criteria at Beginning and End of Each Phase.

| Horse # | History A-0 | Lameness A-0 | Lameness A-28 | Lameness B-28 | Flexion A-0 | Flexion A-28 | Flexion B-28 | Flexion A-0 | Flexion A-28 | Flexion B-28 |
|---|---|---|---|---|---|---|---|---|---|---|
| 1 | + | + | nc* | nc | − | − | − | − | nc | nc |
| 2 | − | + | i | nc | − | − | − | 0 | nc | nc |
| 3 | + | + | nc | nc | + | + | + | + | nc | nc |
| 4 | + | + | nc | nc | + | + | + | + | nc | nc |
| 5 | + | −/+ | i | nc | + | + | − | + | w | i |

(+, − indicates observed or not observed, "i" indicates improved, "nc" indicates no change and "w" indicates worse.)

In all statistical analyses reported herein, paired differences were determined for each variable for each horse by subtracting the value of the variable at day 14 from the value at Day 0 (Diff1), Day 28 from Day 0 (Diff2), and Day 28 from Day 14 (Diff3). Proc T test was then used to compare the means of the treated group and the control group. Affected and unaffected limbs were compared using the same method. A 5% confidence level was used to test for significant differences between groups. Data was reported as mean percent changes in parameters over time within treatment and control groups.

Blood was collected for assessment of serum glycosaminoglycans (SeGAGs) on days 0, 14 and 28 of phases A and B. Horses were sampled by jugular puncture, and blood was aspirated into one 10 ml silicone coated vacuum tube. Samples were centrifuged for 15 min at 1500 rpm, and serum was frozen at −13° C. until analysis. GAGs were quantified by dimethyl methylene blue staining assay—see Alwan et. al., 1991. This is a spectrophotometric assay which uses the conjugation of 1,9-dimethyl methylene blue to GAGs and the absorbance is compared with that of a chondroitin sulfate standard.

GAGs are the major precursors to proteoglycans, which form the basis for cartilage matrix. Increased production of GAGs may indicate that articular proteoglycans are being manufactured from free GAGs. Results from the present experiments indicated a clear trend towards increase in SeGAG levels, as shown in FIG. 1, a plot of % change in Serum GAG against sampling interval.

To determine blood profiles, on days 0 and 28, blood was collected from the animals. Horses were sampled by jugular puncture, and blood was aspired with 10 ml silicone coated vacuum tubes, together with one 7 ml heparin/EDTA tube, to be analyzed for complete blood count.

(CBC: WBC, RBC, Hb, HCT, MCV, MCH, MCHC, RDW, Platelets, MPV, T.S. Protein, Segmented Neutrophil Count, Lymphocyte Count, Monocyte Count, Eosinophil Court, Basophil Count, Anisoytosis Rouleaux, Creanted, Poikilocytosis) and equine serum profile (ESP: GLDH, Creatinine Kinase, Haptoglobin, AST, Gamma-GT, Free Bilirubin, Alkaline Phosphatase, Conjugated Bilirubin, Total Biliruin, Glucose, Cholesterol, Creatinine, Urea, Sodium, Phosphorus, Total Protein, Calcium, Albumin, Globulin, A:G Ratio, Potassium, Carbon Dioxide, Chloride). This was performed in order to identify any possible non-related systemic- or side-effects. CBC was run on Technicon H*1 (Bayer Corp., Etobicoke, Ontario). ESP was run through the Hitachi 911 Biochemical Analyzer (Boehringer Mannheim, Laval, Quebec).

The Complete Blood Count was statistically unremarkable, with no significant differences in any of the hematological parameters examined. Similarly, analysis of Equine Serum Profile showed no significant differences in biochemical profiles of horses on treatment or placebo. These results indicate lack of adverse side affects from the treatments according to the invention.

Synovial fluid was collected from horses on Day 0, 14 and 28 of Phases A and B. Horses received 0.02 mg/kgBW of intravenous xylazine (Anased Injectable; Lloyd Laboratories; Shanandoah, Iowa). The arthritic joint and the corresponding opposite joint were surgically scrubbed. Synovial fluid samples were extracted by aseptic arthrocentesis, and collected in sterile silicone coated blood tubes.

The volume of synovial fluid sample extracted from each horse varied across each sampling period. When the quantity of synovial fluid permitted, cytological analysis was performed on fresh samples. 200 microlitres of fluid was spun in a cytocentrifugal (Shandon Cytospin 11; Shandon Inc.; Pittsburgh, Pa.) at 1,000 rpm for 6 minutes, and resulting slides were stained with a Wright Hemastain (Technicon H*1; Bayer Corp.; Etobicoke, Ontario) and fixed with xylol (animal Health Laboratories, University of Guelph). From the smears, cellularity was determined as high, normal, or low. Cell differentials were ascertained, as were the presence or absence of red blood cells and polarized particles (cartilage fragments). The remaining synovial fluid sample were centrifuged at 1500 rpm for 15 minutes in order to precipitate cellular debris. They were frozen at −13° C. and, upon completion of both sampling periods, were shipped on ice to the Equine Orthopaedic Research Laboratory, Colorado State University. There they were analyzed for prostaglandin $E_2$ ($PGE_2$).

$PGE_2$ was quantified by an extraction process, followed by an ELISA assay with a commercially available kit (TiterZyme Prostaglandin E2—catalog #8-6801N, PerSeptive Biosystems, Framingham, Mass.).

There was a statistically significant increase in overall $PGE_2$ levels during the control phase from Day 0–14 ($p<0.05$). During the same period, $PGE_2$ did not increase significantly when horses received the experimental composition. During the first 14 days, there were no statistically significant differences between arthritic and normal limbs regardless of treatment, but trends again were observed. A 41.3% increase in $PGE_2$ levels in composition-treated, arthritic limbs were accompanied by a 91.7% increase in placebo-treated, arthritic limbs. There was no different between composition and control in normal limbs. Although increases in $PGE_2$ levels in the control arthritic joint were not statistically significant by the $28^{th}$ day, the average increase in the composition treated arthritic joint was only 7.7% whereas in the control joint $PGE_2$ was still increased by 36.9%.

The results are shown on the accompanying FIG. 2.

Thus, supplementation with a formulation according to the invention, in arthritic horses, in the current study resulted in a reduction of $PGE_2$ production in arthritic joints in horses during the first two weeks of supplementation. This observation could explain the anecdotal testimonials to the efficacy of the compositions according to the invention in the management of OA in horses.

Hyaluronic acid HA, the viscous material in synovial fluid, was quantified using the Alcian blue spectrophotometric assay, as described in Smith et. al., 1980. This makes use of a precipitate of Alcian Blue and hyaluronic acid, and the resulting optical density is spectrophotometrically determined.

There were no differences in HA levels between treatment and control phases within horses. Theses results are shown in FIG. 3. This demonstrates that the action of the formulation according to the invention is not an effect on HA.

Formulations as described herein have also been fed to dogs, in quantities pro-rated to account for body weight, resulting in visible improvement in arthritic conditions during and subsequent to the 21–28 day treatment period.

What is claimed is:

1. A herbal based formulation for administration to mammals to alleviate symptoms of arthritis, and comprising an intimate admixture of at least two different plant ingredients, said plant ingredients being an effective amount of a plant material providing a rich source of harpagosides, and an effective amount of a plant material providing a rich source of allantoin.

2. The formulation of claim 1 wherein the plant material providing the rich source of harpagosides is *harpagophytum* (devils claw).

3. The formulation of claim 1 wherein the plant material providing the rich source of allantoin is *Symphytum officinalis* (comfrey).

4. The formulation of claim 1 comprising from about 10–30 parts by weight of devil's claw and from about 10–30 parts by weight of comfrey.

5. A herbal based formulation according to claim 1 further including an effective amount of a plant material providing a rich source of steroidal saponins, and an effective amount of a plant material from the plant Boswellia.

6. The formulation of claim 5 wherein the source of steroidal saponins is *schidegara* (yucca).

7. The formulation of claim 6 comprising from about 10–30 parts by weight of devil's claw, from about 10–30 parts by weight of comfrey, from about 5–10 parts by weight of yucca, and from about 5–20 parts by weight of Boswellia.

8. A herbal based formulation according to claim 1 further including an effective amount of a plant material providing a rich source of taraxacin and sterols, an effective amount of a plant material providing a rich source of glycosides, and an effective amount of a plant material providing a rich source of histamines.

9. The herbal formulation of claim 8 wherein the plant material providing the rich source of taraxacin and sterols is *Taraxacum officinalis* (dandelion).

10. The herbal formulation of claim 9 wherein the plant material providing the rich source of glycosides is *Articum lappa* (burdock).

11. The herbal formulation of claim 10 wherein the plant material providing the rich source of histamines is *Urtica dioica* (nettles).

12. The herbal formulation of claim 11 comprising from about 10–30 parts by weight of devil's claw, from about 10–30 parts by weight of comfrey, from about 10–30 parts by weight of dandelion, from about 10–30 parts by weight of burdock and from about 10–30 parts by weight of nettles.

13. The herbal formulation of claim 12 wherein the devil's claw portion thereof is derived from the tuber of the plant.

14. The herbal formulation of claim 13 wherein the comfrey portion thereof is derived from the leaves of the plant.

15. The herbal formulation of claim 14 wherein the dandelion portion thereof is derived from the leaves and the roots of the plant.

16. The herbal formulation of claim 15 wherein the burdock portion thereof is derived from the whole burdock plant.

17. A herbal formulation according to claim 16 comprising substantially equal amounts by weight of each of the five plant-derived ingredients.

18. A process of alleviating the symptoms of osteoarthritis in equine and canine patients, which comprises administering to the patients an effective amount of a herbal formulation as defined in claim 12.

19. A process of alleviating the symptoms of osteoarthritis in equine and canine patients, which comprises administering tp the patients an effective amount of a herbal formulation as defined in claim 17.

* * * * *